(12) United States Patent
Villa et al.

(10) Patent No.: US 6,194,584 B1
(45) Date of Patent: Feb. 27, 2001

(54) PROCESS FOR PREPARING TRIAZOLE ANTIMYCOTIC COMPOUNDS

(75) Inventors: Marco Villa; Mauro Napoletano, both of Milan; Aldo Belli, Cornate d'Adda; Francesco Ponzini; Fabio Rondina, both of Milan, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/555,503

(22) PCT Filed: Nov. 20, 1998

(86) PCT No.: PCT/EP98/07480

§ 371 Date: Jun. 2, 2000

§ 102(e) Date: Jun. 2, 2000

(87) PCT Pub. No.: WO99/29675

PCT Pub. Date: Jun. 17, 1999

(30) Foreign Application Priority Data

Dec. 5, 1997  (IT) .............................................. MI97A2697

(51) Int. Cl.[7] .................................................. C07D 249/08
(52) U.S. Cl. .......................................................... 548/268.6
(58) Field of Search ............................................ 548/268.6

(56) References Cited

FOREIGN PATENT DOCUMENTS

| 0 315 946 | 5/1989 | (EP) . |
|---|---|---|
| 0 363 582 | 4/1990 | (EP) . |
| 0 667 346 | 8/1995 | (EP) . |
| WO 96 31490 | 10/1996 | (WO) . |
| WO 97 31903 | 9/1997 | (WO) . |

OTHER PUBLICATIONS

Erdik, E., "Copper(I) Catalyzed Reactions of Organolithiums and Grignard Reagents", Tetrahedron, vol. 40, 1984, pp. 641–657.

R.J.K. Taylor, "Organocopper Reagents", 1994, Oxford University Press, Oxford.

March, J., "Advanced Organic Chemistry", 1985, J. Wiley & Sons., Chichester.

Tanaka, T. et al., "Triazole Antifungals. V. Synthesis and Antifungal Activity of Some Amides Related to 3–Acylamino–2–aryl–1–triazolyl–2–butanol" Chem. Pharm. Bull., vol. 40, No. 3, 1992, pp. 661–665.

Xianming, H. et al., "Phase–Transfer Synthesis of Optically Pure Oxetanes Obtained from 1,2,2–Trisubstituted 1,3–Propandiols", Synthesis, May 1995, pp. 533–538.

*Primary Examiner*—Patricia L. Morris
(74) *Attorney, Agent, or Firm*—Arent, Fox, Kintner, Plotkin & Kahn

(57) ABSTRACT

Process for the preparation of a compound of formula (VII) wherein $R_1$ is Cl, F or $CF_3$; $R_2$ is H, Cl, F or $CF_3$; and $R_3$ is $C_{1-4}$ alkyl; characterized in that an olefin of formula (II) is epoxidized to give an oxirane of formula (III) which treated with alkyl-magnesium halide gives a triol of formula (IV) which is turned into an epoxide of formula (V), then treated with 1,2,4-triazole. The compounds (VII) are useful for preparing azole derivatives active as antifungal agent.

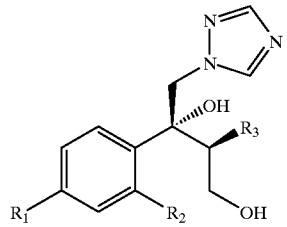

(VII)

2 Claims, No Drawings

PROCESS FOR PREPARING TRIAZOLE ANTIMYCOTIC COMPOUNDS

This is a 371 of International Application Ser. No. PCT/EP98/07480, filed Nov. 20, 1998.

The present invention refers to a process for the preparation of azole compounds endowed with antimycotic activity.

The compounds of formula I

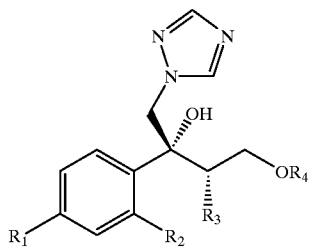

(I)

wherein $R_1$ is chlorine, fluorine or trifluoromethyl, $R_2$ is hydrogen, chlorine, fluorine or trifluoromethyl;

$R_3$ is $C_{1-4}$ alkyl; and $R_4$ is a $C_{1-5}$ polyfluoroalkyl group containing at least two fluorine atoms and optionally other halogen atoms selected from chlorine and bromine;

and their salts with pharmaceutically acceptable acids, are known as antimycotic and antifungal agents.

The patent application WO 97/31903 (in the Applicant's name) shows a class of compounds which those of formula I above fall within, as broad spectrum antimycotics against human and animal pathogenic fungi. Such compounds are obtained from the intermediate of formula VII

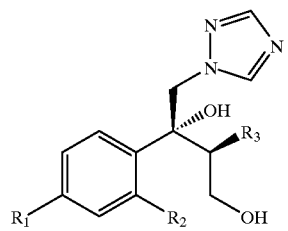

(VII)

wherein $R_1$, $R_2$ and $R_3$ are as defined above, which reacted with the suitable polyfluoroalkyl derivative provides the desired compound of formula I.

It has been now found a new method for preparing the compounds of formula VII constituting an alternative to the synthetic routes described in the above cited prior art.

Therefore the present invention refers to a method for preparing compounds of formula VII as illustrated hereinbelow.

The synthesis of the compounds I according to the invention starts from the olefin of formula II

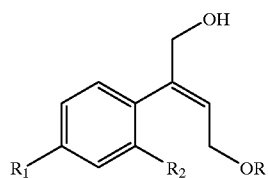

(II)

wherein $R_1$ and $R_2$ are as defined above, and R is hydrogen or a protecting group for the hydroxy moiety. This compound is described and claimed per se in the co-pending patent application filed in the same date of the present one by the Applicant. It is epoxidized, for example according to what described in the patent EP-0 046 033 (in the name of Standford University) which uses titanium alcoholate in the presence of a suitable derivative of tartaric acid and of an organic hydroperoxide, for example tert.butyl- or cumyl-hydroperoxide, or according to what taught in Synthesis, 1986, page 89. It is thus obtained the oxirane of formula III

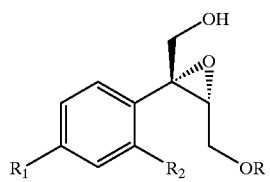

(III)

wherein R, $R_1$ and $R_2$ are as defined above, which, treated with ($C_{1-4}$)alkyl-magnesium halide in the presence of copper (I) iodide, prepared according to what described in *Organocopper Reagents: a practical approach*, page 39. ed. R. I. K Taylor, provides the triol of formula IV

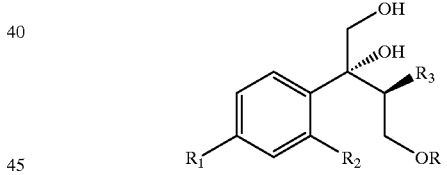

(IV)

wherein R, $R_1$, $R_2$ and $R_3$ are as defined above.

The triol of formula IV is treated with a sulfonic acid chloride, such as, for example methansulfonyl-chloride or tosyl chloride, or with a halogenating agent such as, for example, phosphorous tribromide, thionyl chloride or phosphorous pentachloride and, sequentially, with a strong base, for example NaOH, to give the compound of formula V

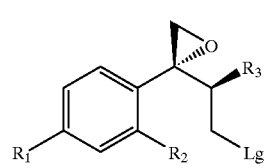

(V)

wherein $R_1$, $R_2$ and $R_3$ are as defined above, and Lg is halogen or a $OSO_2R^{IV}$ group wherein $R^{IV}$ is a ($C_{1-4}$)alkyl or an optionally methyl-substituted phenyl group, which subdued to a reaction for substituting the leaving group Lg according to known methods gives the compound of formula VI

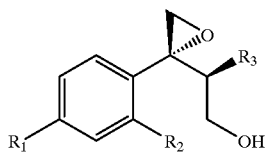

(VI)

wherein $R_1$, $R_2$ and $R_3$ are as defined above. This is treated with 1,2,4-triazole in basic medium to give the desired compound of formula VII.

Hereinbelow fulfilment examples of the present invention are provided.

EXAMPLE 1

Synthesis of (E)-(2R,3R)-2-(2,4-dichlorophenyl)-2,3-dihydroxymethyl-oxirane

A suspension of previously ground 4Å molecular sieves (2.4 g) and (–)-diethyl tartrate (3.4 g; 16.3 mmoles) in methylene chloride (150 ml) was cooled to –20° C. under nitrogen, then treated with titanium isopropylate (3.9 g; 13.6 mmoles) and (E)-2-(2,4-dichlorophenyl)-buten-1,4-diol (3.2 g; 13.6 mmoles). Keeping the temperature at –20° C. 2M tert.-butyl hydroperoxide in methylene chloride (13.5 ml; 27 mmoles) was slowly added in about 30 minutes and it was stirred at –20° C. for further 20 hours. Then 10% sodium sulfite (35 ml; 28 mmoles) was added, the phases were separated and the aqueous one extracted with methylene chloride (30 ml). The joined organic phases were filtered on celite cake and concentrated to half the volume. It was cooled to 0° C., a 30% solution of sodium hydroxide (20 ml) saturated with NaCl was added. The stirring was kept on for 1 hour. The mixture was acidified with 50% $H_2SO_4$, and the organic phase was dried to give 2.9 g of crude. After purification by flash chromatography ($SiO_2$; hexane/ethyl acetate/methanol 70/30/2) 2.63 g of (E)-(2R,3R)-2-(2,4-dichlorophenyl)2,3-dihydroxymethyl-oxirane were obtained (yield 78%; enantiomeric excess: 97.8%).

EXAMPLE 2

Synthesis of (E)-(2R,3 R)-2-(2,4-dichlorophenyl)-2,3-dihydroxymethy-oxirane

Starting from 1 g (4.18 mmoles) of (E)-2-(2,4-dichlorophenyl)-buten-1,4-diol and operating as described in example 1, but using (–)diethyl tartrate and titanium isopropylate in catalytic amounts with respect to (E)-2-(2,4-dichlorophenyl)-buten-1,4-diol, respectively 6% and 5% molar, and with a longer reaction time (about 70 hours), 800 mg of (E)-(2R,3R)-2-(2,4-dichlorophenyl)-2,3-dihydroxymethyl-oxirane were obtained (yield 76.2%, enantiomeric excess 68%) after purification by column chromatography ($SiO_2$; ethyl acetate:petrolatum 1:1).

$^1$H-NMR (300 MHz, DMSO, δ=ppm, J=Hz): 2.74 (ddd, 1H, J=12.2, J=7.6, J=5.6); 3.45 (dd, 1H, J=7.6, J=2.5); 3.54 (dd, 1H, J=12.6, J=6.5); 3.58 (ddd, 1H, J=12.2, J=2.5, J=5.6); 3.88 (dd, 1H, J=12.6, J=6.5); 4.89 (t, 1H, J=5.6); 5.06 (t, 1H, J=6.5); 7.38 (d, 1H, J=8.3); 7.45 (dd, 1H, J=8.3, J=2.0); 7.6 (d, 1H, J=2.0).

EXAMPLE 3

Synthesis of (2R,3S)-2-(2,4-dichlorophenyl)-3-methyl-1,2,4-trihydroxy-butane

A suspension of copper(I) iodide (2.75 g; 14.45 mmoles) in dry THF (360 ml) and cooled to –10° C. was added with a solution of 3M methyl-magnesium chloride in THF (48.2 ml; 144.5 mmoles) then dropwise added, in about 1 hour, with a solution of (E)-(2R,3R)-2-(2,4-dichlorophenyl)-2,3-dihydroxymethyl-oxirane obtained as described in example 1 or 2 (6 g; 24.1 mmoles) keeping the temperature at –10° C. The temperature was left to raise up to +5° C. and it was stirred for 120 hours. The mixture was poured into a saturated solution of ammonium chloride (350 ml), the phases were separated and the aqueous one extracted with ether (100 ml). The organic phases were washed with a saturated solution of NaCl (200 ml), dried over dry $Na_2SO_4$ and evaporated. The crude was purified by flash chromatography ($SiO_2$; n-heptane/ethyl acetate 60/40) to give 3.75 g of (2R,3S)-2-(2,4-dichlorophenyl)-3-methyl-1,2,4-trihydroxy-butane (yield 58%; enantiomeric excess: 97% ).

$^1$H-NMR (300 MHz, DMSO, δ=ppm, J=Hz): 0.55 (d, 3H, J=7.00); 2.47 (ddq, 1H, J=6.30, J=4.80, J=7.00); 3.38 (ddd, 1H, J=11.00, J=4.84, J=6.30); 3.68 (ddd, 1H, J=11.00, J=4.80, J=4.76); 3.86 (dd, 1H, J=11.35, J=4.39); 4.18 (dd, 1H, J=11.35, J=6.23); 4.58 (dd, 1H, J=6.23, J=4.39); 4.70 (dd, 1H, J=4.84, J=4.76); 5.00 (s,1H); 7.38 (dd,1H,J=8.80, J=2.20); 7.47 (d,1H,J=2.20); 7.76 (d,1H,J=8.80).

EXAMPLE 4

Synthesis of (2R)-2-[(2R)-2-(2,4-dichlorophenyl)-oxiranyl]-1-propyl methansulfonate A solution of (2R,3S)-2-(2,4-dichlorophenyl)-3-methyl-1,2,4-trihydroxy-butane obtained as in example 3 (1 g; 3.77 mmoles) in pyridine (20 ml) was added, under stirring in about 30 minutes at a temperature of 15° C., with methansulfonyl chloride (0.91 g; 7.92 mmoles), then the stirring was kept on at 15° C. for 20 hours. The reaction mixture was added with a 10N solution of sodium hydroxide (2 ml; 20 mmoles), and the whole was heated to 35° C. under stirring for 1 hour. Then it was poured into ice (about 80 g), acidified with 50% $H_2SO_4$ (about 35 ml) and twice extracted with methylene chloride (30 ml). The joined organic phases were dried. The crude (1.23 g) was purified by flash chromatography ($SiO_2$; n-heptane/ethyl acetate 85/15) to give 0.96 g of (2R)-2-[(2R)-2-(2,4-dichlorophenyl)-oxiranyl]-1-propyl methansulfonate (yield 78%).

$^1$H-NMR (300 MHz, DMSO, δ=ppm, J=Hz): 0.94 (d, 3H, J=7.03); 2.50 (ddq, 1H, J=6.40, J=6.10, J=7.00); 2.82 (d, 1H, J=4.40); 3.19 (s, 3H); 3.24 (d, 1H, J=4.40); 4.1 (dd, 1H, J=10.25, J=6.10); 4.12 (dd, 1H, J=10.25, J=6.40); 7.46 (m, 3H); 7.66 (d, 1H, J=1.65).

EXAMPLE 5

Synthesis of (2R)-2-[(2R)-2-(2,4-dichlorophenyl)-oxiranyl]-1-propanol

A solution of (2R)-2-[(2R)-2-(2,4-dichlorophenyl)-oxiranyl]-1-propyl methansulfonate obtained as described in example 4 (0.9 g; 2.77 mmoles) in DMF (12 ml) was added with potassium acetate (710 mg; 7.25 mmoles) and tetrabutylammonium iodide (45 mg; 0.14 mmoles) then heated to 75° C. for 4 hours. Another portion of tetrabutylammonium iodide (45 mg; 0.14 mmoles) was added and it was stirred at 75° C. for total 18 hours. After cooling to 20° C., water (1 ml) and 30% NaOH (0.4 ml; 4 mmoles) were added and the stirring was kept on at 20° C. for 1 hour. It was diluted with water (50 ml) and extracted with ether (20 ml). After separation of the phases it was anhydrified over dry $Na_2SO_4$ and dried. The crude (0.7 g) was purified by flash chromatography ($SiO_2$; hexane/ethyl acetate 85/15) to give 0.57 g of (2R)-2[(2R)-2-(2,4-dichlorophenyl)-oxiranyl]-1-propanol (yield 83%).

$^1$H-NMR (300 MHz, DMSO, δ=ppm, J=Hz): 0.83(d,3H, J=6.80); 2.15(ddq,1H, J=6.60, J=6.10, J=6.80); 2.72(d,1H, J=4.70); 3.17(dd(d 1H, J=11.00, J=6.60, J=5.30); 3.22(d,1H, J=4.70); 3.38(ddd,1H, J=11.00, J=6.10, J=5.30); 4.8(t,1H, J=5.30); 7.43(s, 2H); 7.61(s, 1H).

EXAMPLE 6

Synthesis of (2R,3S)-2-(2,4-dichlorophenyl)-3-methyl-1-(1H-1,2,4-triazol-1-yl)-2,4-butandiol A solution of 1,2,4-triazole (0.65 g; 9.4 mmoles) in DMF (7 ml) was portionwise added, at 15–20° C., with 60% NaH (370 mg; 9.4 mmoles). At the end of the addition, the stirring was kept on until total dissolution. A solution of ($^2$R)-2-[(2R)-2-(2,4-dichlorophenyl)-oxiranyl]-1-propanol obtained as described in example 5 (0.62 g; 2.34 mmoles) in DMF (2.5 ml) was added and heated to 125° C. for 2 hours. The mixture was cooled, diluted with water (50 ml) and twice extracted with ethyl acetate (30 ml). The organic phases were washed with water (30 ml), anhydrified over dry Na$_2$SO$_4$, then dried. The crude (0.7 g) was purified by flash chromatography (SiO$_2$; hexane/ethyl acetate/methanol 70/30/10) to give 0.57 g of (2R,3S)-2-(2,4-dichlorophenyl)-3-methyl-1-(1H-1,2,4-triazol-1-yl)-2,4-butandiol (yield 77%), then crystallized from isopropyl ether/toluene 8/2. m.p. 115–116° C. enantiomeric excess: 97%.

$^1$H-NMR (300 MHz, DMSO, δ=ppm, J=Hz): 0.56(d, 3H, J=7.00); 2.86(ddq, 1H, J=5.60, J=5.30, J=7.00); 3.58(ddd, 1H, J=11.00, J-=5.30, J=5.00); 3.83(ddd, 1H, J=11.00, J=5.60, J=5.00); 4.78(d, 1H, J=4.60); 5.05 (t, 1H, J=5.00); 5.2 (d, 1H, J=4.60); 5.63 (s, 1H); 7.2 (dd, 1H, J=8.60, J=2.20); 7.36 (d, 1H, J=8.60); 7.47 (d. 1H, J=2.20); 7.7 (s, 1H); 8.25 (s, 1H).

What is claimed is:

1. Process for the preparation of a compound of formula VII

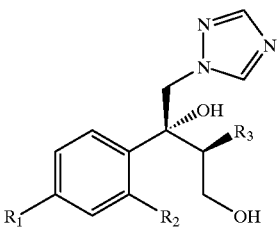

wherein R$_1$ is chlorine, fluorine or trifluoromethyl;
R$_2$ is hydrogen, chlorine, fluorine or trifluoromethyl;
R$_3$ is C$_{1-4}$ alkyl; characterized in that an olefin of formula

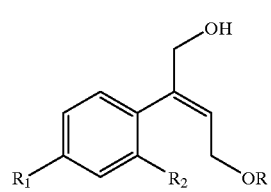

wherein R$_1$ and R$_2$ are as defined above, and R is hydrogen or a protecting group of the hydroxy moiety, is epoxidized to give the oxirane of III

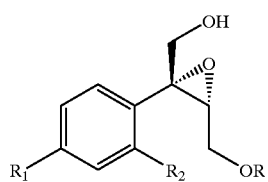

wherein R, R$_1$ and R$_2$ are as defined above, which, treated with (C$_{1-4}$)alkyl-magnesium halide in the presence of copper(I) iodide gives a triol of formula IV

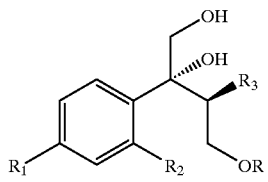

wherein R, R$_1$, R$_2$ and R$_3$ are as defined above; and characterized in that the triol of formula IV is treated with a sulfonic acid chloride or with a halogenating agent, then with a strong base, to give the compound of formula V

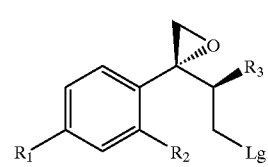

wherein R$_1$, R$_2$ and R$_3$ are as defined above, and Lg is halogen or a OSO$_2$R$^{IV}$ group wherein in R$^{IV}$ is a (C$_{1-4}$)alkyl group or an optionally methyl-substituted phenyl group, which is subdued to a reaction for substituting the Lg leaving group thus yielding the compound of formula VI

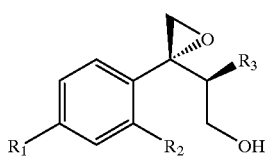

wherein R$_1$, R$_2$ and R$_3$ are as defined above, which is treated with 1,2,4-triazole in basic medium and gives the compound of formula VII.

2. Process for the preparation of a compound of formula I

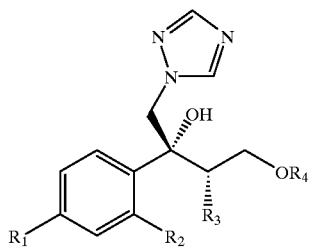
(I)

wherein $R_1$ is chlorine, fluorine or trifluoromethyl;

$R_2$ is hydrogen, chlorine, fluorine or trifluoromethyl;

$R_3$ is $C_{1-4}$ alkyl; and $R_4$ is a $C_{1-5}$ polyfluoroalkyl group containing at least two fluorine atoms and optionally other halogen atoms selected from chlorine and bromine;

and their salts with pharmaceutically acceptable acid, characterized in that an olefin of formula II

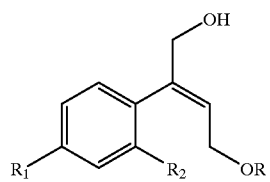
(II)

wherein $R_1$ and $R_2$ are as defined in claim 1, and R is hydrogen or a protecting group of the hydroxy moiety, is epoxidized to give the oxirane of III

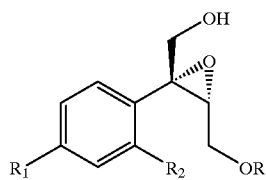
(III)

wherein R, $R_1$ and $R_2$ are as defined in claim 1, which, treated with $(C_{1-4})$alkyl-magnesium halide in the presence of copper(I) iodide gives a triol of formula IV

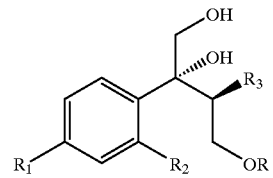
(IV)

wherein R, $R_1$, $R_2$ and $R_3$ are as defined in claim 1; and characterized in that the triol of formula IV is treated with a sulfonic acid chloride or with a halogenating agent, then with a strong base, to give the compound of formula V

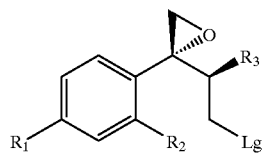
(V)

wherein $R_1$, $R_2$ and $R_3$ are as defined in claim 1 and Lg is halogen or a $OSO_2R^{IV}$ group wherein $R^{IV}$ is a $(C_4)$alkyl group or an optionally methyl-substituted phenyl group, which is subdued to a reaction for substituting the Lg leaving group thus yielding the compound of formula VI

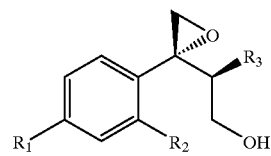
(VI)

wherein $R_1$, $R_2$ and $R_3$ are as defined in claim 1, which is treated with 1,2,4-triazole in basic medium and gives the compound of formula VII

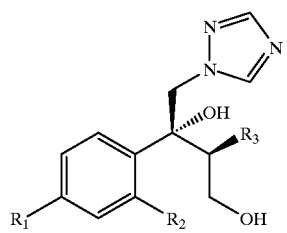
(VII)

wherein $R_1$, $R_2$ and $R_3$ are as defined in claim 1, which is reacted with the suitable polyfluoroalkyl derivative.

* * * * *